United States Patent [19]

Kendrick

[11] Patent Number: 5,582,592
[45] Date of Patent: Dec. 10, 1996

[54] TOPICAL APPLICATION OF STEROID HORMONES AND VAGINOCERVICAL STIMULATION TO INDUCE MATERNAL BEHAVIOR OF ANIMALS

[75] Inventor: Keith M. Kendrick, Linton, United Kingdom

[73] Assignee: Ministry of Agriculture, Fisheries and Food, London, United Kingdom

[21] Appl. No.: 170,195

[22] PCT Filed: Jun. 22, 1992

[86] PCT No.: PCT/GB92/01127

§ 371 Date: May 27, 1994

§ 102(e) Date: May 27, 1994

[87] PCT Pub. No.: WO93/00096

PCT Pub. Date: Jan. 7, 1993

[30] Foreign Application Priority Data

Jun. 25, 1991 [GB] United Kingdom .................. 9113726

[51] Int. Cl.$^6$ .................................................. A61M 31/00
[52] U.S. Cl. ........................... 604/55; 604/290; 128/898
[58] Field of Search .................................. 604/55, 10–15, 604/49, 906, 285–290; 600/33, 35; 424/430–433, DIG. 15; 514/967, 899, 843; 128/830, 898

[56] References Cited

U.S. PATENT DOCUMENTS 4,629,449  12/1986  Wong ........................................ 604/55

FOREIGN PATENT DOCUMENTS 166990  1/1974  New Zealand .
215635  10/1989  New Zealand .

OTHER PUBLICATIONS

Davis et al; J. Dairy Science 66; Feb. 24, 1982; *Induction of Lactation in Non–Pregnant Cows* . . . , pp. 450–457.
Keverne et al; (1991); *Morphine and Corticotropin Releasing Factor* . . . , Brain Research 540, pp. 55–62.
Kendrick, K. M. & E. B. Beverne (1987); Intracerebroventricular oxytocin stimulates maternal behavious in the sheep; Neuroendocrinology 46: pp. 56–61.
Kendrick, K. M. & E. B. Keverne (1989); Effects of intracerebroventricular infusions of naltrexone and phentolamine . . . ; Brain Research 505: pp. 329–332.
Kendrick, K. M., F. Levy & E. B. Keverne; Importance of vaginocervical stimulation for the formation . . . ; Physiology and Behavior 50: pp. 595–600, 1991.
Kendrick, K. M., E. B. Keverne, B. A. Baldwin & D. F. Sharman (1986); Cerebrospinal fluid levels of acetylcholinesterase . . . ; Neuroendocrinology 44: pp. 149–156.
Kendrick, K. M., E. B. Keverne, M. R. Hinton & J. A. Goode; (1991); Cerebrospinal and plasma concentrations . . . ; Brain Research Bulletin 26: pp. 803–807.
Kendrick, K. M. E. B. Keverne, C. Chapman & B. A. Baldwin (1988); Intracranial dialysis measurement of oxytocin, monoamine . . . ; Brain Research 439; pp. 1–10.
Kendrick, K. M., E. B. Keverne, M. R. Hinton & J. A. Goode; Oxytocin, amino acid and monoamine release in the medical preoptic area . . . ; Brain Research (in press).
Kendrick, K. M., F. Levy & E. B. Keverne (1991); Neurochemical changes underlying the formation of olfactory . . . ; Current Separations 10: pp. 96–97.
Kendrick, K. M. & E. B. Keverne; Control of synthesis and release of oxytocin in the sheep brain; Annals of the New York Academy of Sciences (in press).

*Primary Examiner*—Randall L. Green
*Assistant Examiner*—V. Alexander
*Attorney, Agent, or Firm*—Jacobson, Price, Holman & Stern, PLLC

[57] ABSTRACT

The invention provides a process of artificially inducing a non-pregnant, non-human female animal to act as a foster mother using a non-invasive method which comprises administering a topical application of at least one steroid hormone to the animal for a period of time sufficient that uptake of hormone by the animal acts both (i) to stimulate lactation and (ii) to prime the animal for vaginal and cervical stimulation so that such stimulation causes induction of maternal behavior. The hormone may be selected from either progestogen or oestrogen or a mixture of the two, and may be applied to the animal via an intra-vaginal sponge by a method comprising the steps of inserting a first hormone impregnated sponge into the vagina of a non-pregnant animal for about two to three weeks; removing the first sponge and replacing it with a second hormone impregnated sponge for a further period of time of about two to four weeks. Maternal behavior is induced by vaginal and cervical stimulation.

19 Claims, No Drawings

TOPICAL APPLICATION OF STEROID HORMONES AND VAGINOCERVICAL STIMULATION TO INDUCE MATERNAL BEHAVIOR OF ANIMALS

The present invention relates to artificial animal foster mothers, and more particularly to a technique for artificially inducing non-pregnant animals to act as foster mothers.

In the field of animal husbandry the rearing of young animals can be a serious problem if there are more young requiring feeding than there are available lactating mothers. In particular, young animals which are orphans or which come from a multiple-birth group of siblings may require fostering. Even if suitable foster mothers are available, the problem of maternal bonding/maternal rejection of foster animals has to be overcome before fostering can be successful.

The present invention can provide suitable foster mothers from the population of non-pregnant female animals and it can provide such foster mothers who exhibit desirable maternal behavior (i.e. bonding to the fostered young animal rather than rejecting it).

The technique of the present invention is now described in detail with reference to the use of ewes to foster lambs, but it is to be understood that the invention in its broadest aspects is not limited to sheep rearing and extends to all mammalian animal species.

BACKGROUND OF THE INVENTION

Each year a number of orphan and triplet lambs have to be reared artificially. The most common method for rearing these animals, in large flocks, is to place them in groups on milk bars without any maternal care. Not only is this procedure costly and labor intensive, but it also deprives the lambs of maternal care which can lead to the development of social and sexual abnormalites in adulthood. Further, animals raised on milk bars cannot derive the full immunization benefit which would normally follow from the antibodies passed on to them through a ewe's milk. It is therefore clearly preferable from a welfare, health and economic standpoint to raise orphan and triplet lambs with proper foster mothers. During the past 7 years we have attempted to establish how lactation and maternal behavior are stimulated in the sheep, and what controls the formation of the selective recognition bond between the ewe and its lambs. The primary aims of this work have been to establish reliable protocols for (a) Fostering orphan lambs onto maternal ewes, to avoid the necessity of rearing them without maternal care on milk bars and (b) To improve poor quality maternal care, particularly in primiparous animals, which also contributes to increased mortality and suffering in lambs. The main approach adopted to provide these protocols has been to investigate the importance of the various physiological changes occurring in sheep during pregnancy, parturition and post-partum for the control of lactation and maternal behavior.

A series of studies has established that in sheep, the primary stimulus for inducing maternal responses towards new born lambs is feedback from the vagina and cervix reaching the brain. Thus, maternal behavior can be induced in non-pregnant sheep simply by mechanically stimulating the vagina and cervix. Conversely, blocking the signals from the vagina and cervix reaching the brain, using epidural anaesthesia, prevents ewes from showing normal post-partum maternal behavior.

The changes in blood concentrations of progesterone and oestradiol which occur during pregnancy are essential for the production of lactation and for the ability of stimulation of the vagina and cervix to induce maternal behavior. These steroids are not however, as had previously been proposed, the major factors controlling the stimulation of this behavior. Maternal experience also plays a role, and we have found that nulliparous ewes are less responsive to the effects of stimulation of the vagina and cervix, following short term treatment with progesterone and/or oestradiol, than multiparous ones, and this may partly explain why primiparous ewes are often poor mothers.

Stimulation of the vagina and cervix during parturition is also important for the formation of the selective olfactory recognition bond between a ewe and its lambs and we have found that artificial mechanical stimulation of these structures can reliably induce ewes to accept and form new recognition bonds with orphan lambs even 24 h post-partum. Importantly, this stimulation of the vagina and cervix does not interfere in any way with the recognition bond already formed with the ewes own lambs and works equally well in maternal multiparous or primiparous ewes.

In a series of studies where we have sampled changes in brain chemistry, which might be associated with the post-partum stimulation of maternal behavior, we have shown that the peptide hormone oxytocin is released in the brain during parturition and following artificial vaginocervical stimulation. This release does not occur when the animals do not show maternal behavior following an epidural anaesthetic block. Furthermore, infusion of this peptide into the brain ventricles stimulates maternal behavior in non-pregnant ewes within 30 s, provided that they are pre-treated with oestradiol. The source of oxytocin within the brain is primarily derived from cells in the brain which do not project to the posterior pituitary. The blood-brain barrier is relatively impermeable to the peptide so that peripheral injections of it, or the high concentrations occurring in the blood at parturition, cannot enter into the brain to exert any behavioral action. We have shown that the oxytocin-containing cells in the sheep brain express oxytocin mRNA and that the levels of mRNA expression are at their highest during parturition and lactatation, when maternal behavior is displayed. Oxytocin mRNA levels and release of oxytocin within the brain are increased following exogenous treatment with progesterone and/or oestradiol, further underlying the important modulatory role that these steroids have on the brain oxytocinergic cells controlling the induction of maternal behavior. We have also found evidence that endogenous opiate pathways in the brain influence both the ability of artificial stimulation of the vagina and cervix to induce maternal behavior and central oxytocin release.

It has been known for many years that the formation of the selective recognition bond between ewes and lambs is olfactory, since rendering ewes anosmic (by removing the olfactory bulbs in the brain) prevents it and they will therefore mother any lambs. Research suggests that noradrenergic and possibly cholinergic pathways are important for the formation of the selective recognition bond. We have recently shown that noradrenaline and acetylcholine are released in the olfactory bulbs during parturition and during induction of fostering of orphan lambs using artificial stimulation of the vagina and cervix. After the establishment of the selective bond, these transmitters are also released following brief exposure to lamb odor. These changes do not occur immediately at parturition in primiparous animals, but after a delay of several hours and this may explain why these animals take longer to form the selective recognition bond with their lambs than multiparous ewes.

Our extensive behavioral and physiological studies have therefore clearly established the importance of the influence of stimulation of the vagina and cervix for mediating profound changes in brain chemistry which alter the behavior of ewes towards lambs. While administration of artificial stimulation of the vagina and cervix is extremely effective in inducing ewes with single lambs to adopt orphan lambs up to 24 h post-partum, this does not provide a total solution for fostering all orphan or triplet lambs since the availability of suitable mothers for fostering is extremely unpredictable. As an alternative solution we have surprisingly found that non-pregnant animals could act as foster mothers. For this approach to be a viable proposition, it is essential that lactation be artificially induced simply, quickly and cheaply; and it is also essential to induce permanent high quality maternal care towards lambs so that they are reared successfully to weaning.

Previous studies inducing lactation in sheep have relied on protocols where steroid hormones or other substances are injected into the animals over long periods. Such procedures are neither practical nor economical for farming. We instead developed a protocol based on topical application of at least one steroid hormone, preferably a combination of a progestogen and an oestrogen such as a combination of progesterone and oestradiol. These hormones are also normally present in high concentrations in the blood during late pregnancy. It is known in current farming practice to use vaginal sponges impregnated steroid for synchronizing oestrous in animals. It is also known (S. R. Davis et al, 1983. J. Dairy Sci. 66:450–457) that it is possible to induce lactation of non-pregnant cows by use of an intravaginal sponge impregnated with 500 mg estradiol-17$\beta$ and 1000 mg progesterone inserted for 10 days and then removed. Treatment with the sponge for 10 days resulted in lactogenesis in 25% of treated cows. Udders of cows induced to lactation by intravaginal sponge (IVS) treatment began to fill with secretion 8 to 10 days after IVS insertion and milking was begun 12 days after insertion (2 days after IVS removal).

SUMMARY OF THE INVENTION

In contrast to the previous techniques, the present invention provides a protocol which not only stimulates lactation but also, provides the best possible priming for stimulation of the vagina and cervix to induce maternal behavior. Topical application of at least one steroid hormone, preferably a combination of hormones, is carried out for a period of time sufficient both (i) to stimulate lactation and (ii) to prime the animal for vaginal and cervical stimulation so that such stimulation causes induction of maternal behavior. The time period proposed according to the invention is relatively long in comparison to that previously used in IVS treatments, e.g. a period of the order of weeks rather than days.

DETAILED DESCRIPTION OF INVENTION

According to the invention, by way of example, ewes were first given vaginal sponges containing 250 mg progesterone (or medroxyprogesterone acetate) and 25 mg $\beta$-oestradiol for 2 weeks. These were then replaced with a second sponge containing 250 mg progesterone and 50 mg $\beta$-oestradiol for a further 2–4 weeks. Twenty two ewes (12 multiparous and 10 yearling/shearling nulliparous) were used. All 12 multiparous ewes and 8/10 multiparous ewes showed significant udder development following these treatments although the size of the udders and the amount of milk produced was approximately one-quarter to one-third of normal pregnant ewes just prior to parturition. The first milk expressed following the treatment also had the coloring and consistency of colostrum.

Twelve of the ewes which showed a good lactation response to the hormone treatment (8 multiparous and 4 nulliparous), but had not been milked, were subsequently presented with lambs ranging from 30 min to 6 days old. None of these animals showed full maternal acceptance of these lambs at this time. The hormone-containing sponges were removed and the ewes were given two minutes of manual stimulation of the vagina and cervix. This stimulation is carried out with the hand sheathed in a sterile glove lubricated with antiseptic cream and comprises rhythmically pushing the hand up into the vagina and exerting pressure on the cervix. The index and middle finger are extended to enter the neck of the cervix and are used to stretch this while the remainder of the hand is moved backwards and forwards within the vagina (our behavioral studies and those on the release of oxytocin within the brain have indicated that this is the most effective method of stimulation). When the hand is removed from the vagina, the head and rump of the lamb are smeared with the secretions on the glove so that the lamb smells familiar to the ewe (this further reduces any possibility of rejection of the lamb). Following this stimulation, all twelve ewes showed immediate intensive maternal behavior towards the lambs and continued to lick them for several hours even though the majority of lambs were not wet with amniotic fluid. All the ewes accepted suckling attempts within this period and the lambs all received milk. The treatment worked equally well in the multiparous and nulliparous animals although 2 out of the 4 nulliparous animals took over an hour before they finally stood to allow the lamb to suckle. All the ewes also objected volubly if their adopted lambs were removed from their pens three hours after fostering, similar to normal mothers. Indeed, the majority of these foster-mothers showed a greater intensity of maternal responses than we have normally seen in post-parturient ewes. This may have been because they had not been through the physical exertions of giving birth and therefore had more energy to expend on maternal responses towards lambs.

In tests carried out 24 h post-fostering, we confirmed that all the animals had formed normal selective recognition bonds with the lambs and rejected lambs other than their own. The sheeps were housed inside for the first four weeks after fostering and by the end of this period the level of lactation had clearly increased in all of them in response to suckling. After one month, the ewes and lambs were put outside and the lambs introduced to creep feed. Although weight gain was initially less in most of the foster lambs than in normally reared individuals, by three months, this weight difference had dissappeared and the weights of the fostered lambs were not significantly different from those of lambs reared by normal lactating ewes during the same period. One of the twelve lambs reared by a multiparous mother died 4 days after fostering (cause unknown), but the remaining eleven remained healthy.

Further experiments on 42 ewes (22 multiparous and 20 nulliparous) have provided the following additional information:

(1) Analysis of the immunoglobulin content of the first milk expressed in ewes with artificially induced lactation showed that this was high and that casein levels were low (giving the milk its yellowish appearance). This data supports our original contention that the treatment stimulates the formation of colostrum and therefore gives the fostered lambs antibody protection. The artificially produced milk also contains the normal milk proteins beta-lactoglobulin and alpha-lactoglobulin. These findings show that ewes with artificially induced lactation could be used as colostrum donors as well as foster mothers. For example, animals could be repeatedly treated to induced lactation and the colostrum produced stored and given to lambs as required (irrespective of whether or not they need to be fostered). Ewes could also be treated with vaccines during the induction of lactation to boost antibody production or to stimulate the production of antibodies against specific life-threatening diseases which normal colostrum fails to protect against.

(2) The reliability of lactation induction, and its level, is slightly improved by adopting a treatment protocol of using a three week treatment with a vaginal sponge or insert containing 250 mg progesterone (or medroxyprogesterone acetate) and 50 mg β-oestradiol (or oestradiol dipropionate) followed by a further three week treatment with a vaginal sponge or insert containing the same concentration of progestogen and double that of the oestrogen. A small further improvement was seen if the concentration of oestrogen was raised to 100 mg in the first sponge/insert and to 250 mg in the second one. All animals receiving these different hormone treatments became maternal to lambs after manual stimulation of the vagina and cervix.

(3) The best results for the induction of lactation were achieved by combining treatment with vaginal sponges/inserts containing 250 mg progesterone (or medroxyprogesterone acetate) and 50 mg β-oestradiol (or oestradiol dipropionate) for three weeks, plus double the oestrogen dose for a further three weeks, with exposure of the animals to 16–20 h of artificial light per day for the whole six week treatment period. The latter treatment increased blood concentrations of the lactogenic hormone, prolactin, compared to the hormone treatments alone. Up to 50% of normal lactation was induced with this approach. All animals receiving this treatment became maternal to lambs after manual stimulation of the vagina and cervix.

(4) No obvious differences between the efficacy of progesterone compared with medroxyprogesterone acetate, or β-oestradiol compared with oestradiol dipropionate, in inducing lactation or a maternal response following stimulation of the vagina and cervix were seen.

This is the first demonstration of a combined method for artificially stimulating lactation and maternal behavior in sheep and it works even in virgin ewes. Indeed, the high blood concentrations of progesterone and oestradiol produced by the sponges probably facilitated the ability of stimulation of the vagina and cervix to induce maternal behavior in these inexperienced animals. The overall protocol is quick, simple and economical and provides a viable alternative to rearing orphan and triplet lambs on milk bars. The farmer need not even sacrifice good breading ewes for creating a foster flock but can instead use yearling/shearling nulliparous ewes. This both ensures that these animals, which otherwise might not be used for breeding, are put to good use and maximizes the chances that, through this experience, they will benefit by showing better maternal responses and be good mothers towards lambs of their own in the subsequent year.

We can conclude therefore that, from the standpoint of welfare, health, economics and efficient use of resources, the use of artificial foster mothers for rearing orphan and triplet lambs provides an attractive alternative to milk bars. A similar approach to the induction of lactation and fostering young is applicable to other mammalian animal species which form selective recognition bonds, including domestic species such as cattle (e.g. cows, buffalo, oxen) goats, horses, camels, pigs and other ungulates. Using 9 multiparous ewes with artificially induced lactation, we have shown that they will mother, and rear, goat kids following artificial vaginocervical stimulation. This finding is important since it raises the possibility that sheep can act as foster mothers to offspring of other related, and potentially more valuable, species. In the case of milking goats, this could provide a means of giving their kids (which have to be removed from them) a maternal upbringing, with a related species, and thereby avoid rearing them on milk bars. Using this approach, sheep could also act as foster mothers to offspring of other ungulate species and this might, for example, be a valuable option for captive breeding of endangered species.

Whereas this invention has been exemplified by the use of particular steroid hormones such as progesterone, medroxyprogesterone, β-oestradiol and oestradiol dipropionate, it is to be understood that it is envisaged that any form of progestogen or oestrogen (either natural or artificial) could be used in appropriate formulations.

The dose ranges and ratios of hormones described herein are illustrative and the man skilled in the art will appreciate that various ranges and ratios would be appropriate for different breeds and different species.

The preferred method of stimulation of maternal behavior is manual, as described before. However, probes for stimulation of the vagina and cervix are already known. With small animals it may be found to be difficult to properly stimulate the vagina and cervix by hand and stimulation may be carried out according to the invention using an appropriate probe. A plastic bodied torpedo-shaped probe with a rubber tip has been successfully used.

The preferred method of topical application of the hormone is by use of IVS. However, it is to be understood that it is envisaged that the invention could be carried out using some other insertable hormone delivery system such as, for example, a hormone impregnated coil. A coiled design of vaginal insert can be used to administer the hormonal treatment just as successfully as by sponge.

It is a particularly important and advantageous feature of the process of the present invention that the necessary interaction with the animal body can be carried out with the desired result by a farmer or technician without specialist medical knowledge and skill. The method of this invention does not involve any invasive or surgical methods such as the injection of hormones into the brain, bloodstream or tissues of the animal.

For the purposes of this description the term "non-pregnant" is used to describe animals which are in a condition which is neither pre-natal nor recent post-natal. Such animals are not naturally lactating nor are they inclined naturally to exhibit maternal behavior.

I claim:

1. A process of artificially inducing a non-pregnant, non-human female animal to act as a foster mother using a non-invasive method which comprises:

(i) inserting a first hormone impregnated intravaginal sponge into the vagina of an animal, wherein the first hormone impregnated sponge comprises at least one steroid hormone;

(ii) removing the first hormone impregnated sponge and inserting a second hormone impregnated sponge into the vagina of the animal from step (i), wherein the second hormone impregnated sponge comprises at least one steroid hormone; and (iii) vaginally and cervically stimulating the animal; wherein the first and second sponges are inserted for a period of time sufficient to induce lactation and so that the stimulation of step (iii) causes induction of maternal behavior.

2. The process according to claim 1, wherein the steroid hormone is selected from either progestogen or oestrogen or a mixture of the two.

3. The process according to claim 1, wherein the first sponge is impregnated with progesterone and β-oestradiol in a 10:1 by weight ratio and the second sponge is impregnated with progesterone and β-oestradiol in a 5:1 by weight ratio.

4. The process according to claim 3, wherein the first sponge contains about 250 mg of progesterone and about 25 mg of β-oestradiol and the second sponge contains about 250 mg of progesterone and about 50 mg of β-oestradiol.

5. The process according to claim 1, which comprises using a three week treatment with a vaginal sponge or insert containing 250 mg progesterone (or medroxyprogesterone acetate) and 50 mg β-oestradiol (oestradiol dipropionate) followed by a further three week treatment with a vaginal sponge or insert containing the same concentration of progestagen and double that of progestogen.

6. The process according to claim 5, modified by using 100 mg oestrogen in the first sponge/insert and by using 250 mg oestrogen in the second sponge/insert.

7. The process according to claim 1, wherein steriod hormone treatment is combined with exposure of the animal to 16–20 hours of artificial light per day during a six week treatment period.

8. The process according to claim 1, wherein the non-pregnant animal is multiparous.

9. The process according to claim 1, wherein the non-pregnant animal is nulliparous.

10. The process according to claim 1, wherein the non-pregnant animal is primiparous.

11. The process according to claim 9, wherein the non-pregnant animal is a virgin.

12. The process according to claim 1, wherein the animal is of an ungulate species.

13. The process according to claim 1, wherein the animal is selected from the group consisting of cow, sheep, buffalo, oxen, goat, horse, pig and camel.

14. The process according to claim 1, wherein maternal behavior is induced by vaginal and cervical stimulation.

15. The process according to claim 14, wherein manual vaginal and cervical stimulation is carried out by rhythmically pushing a hand up into the vaginal and exerting pressure on the cervix.

16. The process according to claim 15, wherein the index and middle finger of the hand are extended to enter the neck of the cervix and are used to stretch the neck of the cervix while the remainder of the hand is moved backwards and forwards within the vagina.

17. The process according to claim 14, wherein maternal behavior is induced by vaginal and cervical stimulation using a probe.

18. The process according to claim 14, wherein a juvenile animal to be fostered is smeared with vaginal secretion from the foster mother animal following the vaginal and cervical stimulation.

19. The process of claim 1 wherein the first sponge is inserted for a period of about two to three weeks and the second sponge is inserted for a period of about two to four weeks.

* * * * *